(12) United States Patent
Osypka et al.

(10) Patent No.: US 9,907,570 B2
(45) Date of Patent: Mar. 6, 2018

(54) STEERABLE MEDICAL DEVICES

(71) Applicant: Oscor Inc., Palm Harbor, FL (US)

(72) Inventors: Thomas P. Osypka, Palm Harbor, FL (US); Michael J. Gelineau, Odessa, FL (US); Paul Chagnon, Palm Harbor, FL (US); Brian Walguarnery, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 661 days.

(21) Appl. No.: 14/455,018

(22) Filed: Aug. 8, 2014

(65) Prior Publication Data

US 2015/0057610 A1   Feb. 26, 2015

Related U.S. Application Data

(60) Provisional application No. 61/886,132, filed on Oct. 3, 2013, provisional application No. 61/869,140, filed on Aug. 23, 2013.

(51) Int. Cl.
*A61B 17/34* (2006.01)
*A61M 25/01* (2006.01)
(Continued)

(52) U.S. Cl.
CPC ...... *A61B 17/3468* (2013.01); *A61B 17/3423* (2013.01); *A61B 90/94* (2016.02); *A61M 25/0136* (2013.01); *A61M 25/0147* (2013.01); *A61B 2017/00305* (2013.01); *A61B 2017/00327* (2013.01); *A61B 2017/00938* (2013.01);
(Continued)

(58) Field of Classification Search
CPC ............ A61B 17/3423; A61B 17/3468; A61B 2017/00305; A61B 2017/00327; A61B 2017/00938; A61B 2017/3425; A61B 2017/3441; A61B 90/94; A61M 25/0136; A61M 25/0147

See application file for complete search history.

(56) References Cited

U.S. PATENT DOCUMENTS 5,215,540 A    6/1993  Anderhub
5,364,352 A    11/1994 Corfitsen et al.
(Continued)

FOREIGN PATENT DOCUMENTS

WO   WO-2012/075156 A1   6/2012
WO   WO-2012/158864 A1   11/2012

OTHER PUBLICATIONS

European Search Report dated Nov. 7, 2014 issued on European Patent Application No. 14180667.9.

*Primary Examiner* — Bhisma Mehta
*Assistant Examiner* — Brandy S Lee
(74) *Attorney, Agent, or Firm* — Locke Lord LLP; Scott D. Wofsy

(57) ABSTRACT

A steerable medical device can include a sheath defining a longitudinal axis having a deflectable distal end portion, and at least one lateral passage extending therethrough and configured to accommodate at least one steering cable and a steering handle operatively associated with a proximal end portion of the sheath and having an actuation mechanism operatively connected to the at least one steering cable accommodated within the at least one lateral passages of the sheath for steering the deflectable distal end portion of the sheath in at least one direction relative to the longitudinal axis thereof.

20 Claims, 15 Drawing Sheets

(51) Int. Cl.
*A61B 90/94* (2016.01)
*A61B 17/00* (2006.01)

(52) U.S. Cl.
CPC .............. *A61B 2017/3425* (2013.01); *A61B 2017/3441* (2013.01)

(56) References Cited

U.S. PATENT DOCUMENTS

| | | | |
|---|---|---|---|
| 5,372,587 A | 12/1994 | Hammerslag et al. | |
| 5,456,664 A | 10/1995 | Heinzelman et al. | |
| 5,462,527 A * | 10/1995 | Stevens-Wright | A61B 18/1492 600/585 |
| 5,792,140 A | 8/1998 | Tu et al. | |
| 5,800,413 A | 9/1998 | Swartz et al. | |
| 5,827,227 A | 10/1998 | DeLago | |
| 5,893,885 A | 4/1999 | Webster, Jr. | |
| 6,004,280 A | 12/1999 | Buck et al. | |
| 6,146,355 A | 11/2000 | Biggs | |
| 6,475,213 B1 | 11/2002 | Whayne et al. | |
| 6,916,306 B1 | 7/2005 | Jenkins et al. | |
| 7,232,422 B2 | 6/2007 | Gibson et al. | |
| 8,348,888 B2 | 1/2013 | Selkee | |
| D708,740 S | 7/2014 | Osypka et al. | |
| 2001/0012946 A1 | 8/2001 | MacKenzie et al. | |
| 2002/0165484 A1 * | 11/2002 | Bowe | A61M 25/0136 604/95.05 |
| 2004/0092962 A1 * | 5/2004 | Thornton | A61B 50/30 606/139 |
| 2005/0192558 A1 * | 9/2005 | Bernard | A61M 25/007 604/525 |
| 2005/0197623 A1 * | 9/2005 | Leeflang | A61M 25/0144 604/95.04 |
| 2005/0234436 A1 | 10/2005 | Baxter et al. | |
| 2006/0030753 A1 | 2/2006 | Boutillette et al. | |
| 2006/0041295 A1 | 2/2006 | Osypka | |
| 2006/0167416 A1 * | 7/2006 | Mathis | A61B 10/0275 604/164.01 |
| 2007/0129747 A1 | 6/2007 | Dorman | |
| 2008/0097386 A1 | 4/2008 | Osypka | |
| 2008/0255540 A1 * | 10/2008 | Selkee | A61M 25/0136 604/528 |
| 2009/0240235 A1 | 9/2009 | Murata | |
| 2010/0106141 A1 | 4/2010 | Osypka et al. | |
| 2010/0191151 A1 | 7/2010 | Kwak | |
| 2011/0306851 A1 | 12/2011 | Wang | |
| 2012/0029510 A1 | 2/2012 | Haverkost | |
| 2012/0116283 A1 | 5/2012 | Nilsson | |
| 2012/0116383 A1 | 5/2012 | Mauch et al. | |
| 2012/0123327 A1 | 5/2012 | Miller | |
| 2013/0304106 A1 | 11/2013 | Breznock | |
| 2015/0045696 A1 | 2/2015 | Osypka | |
| 2015/0057655 A1 | 2/2015 | Osypka | |

* cited by examiner

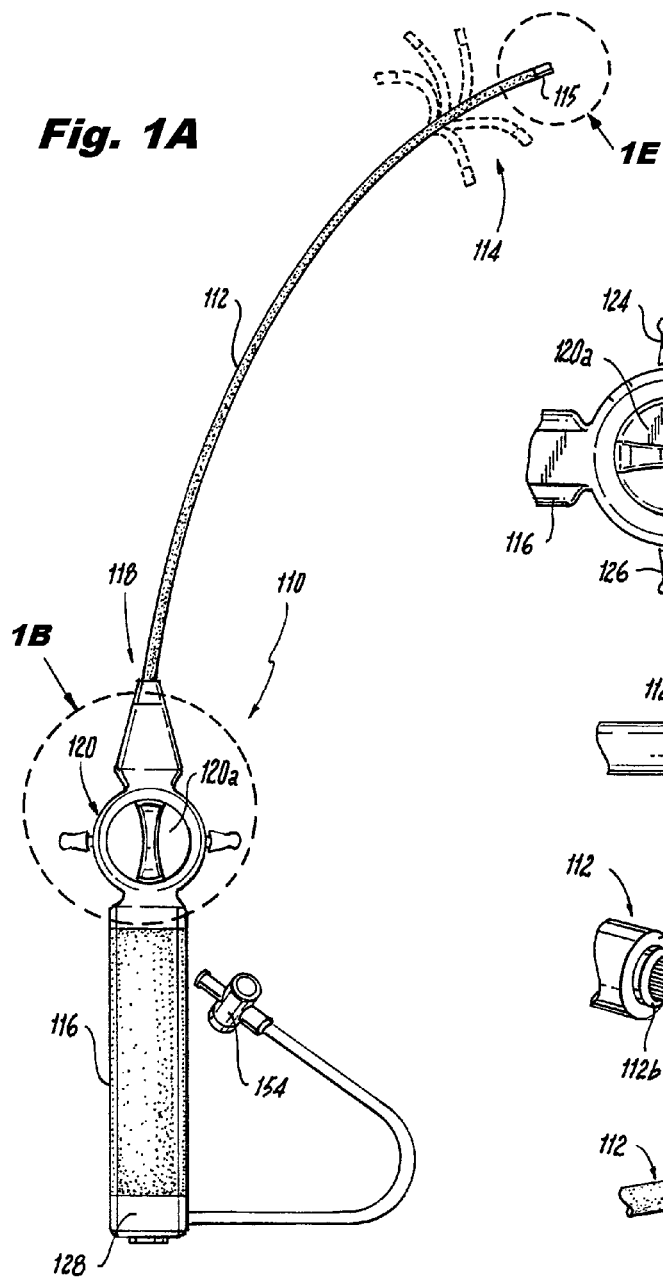
Fig. 1A
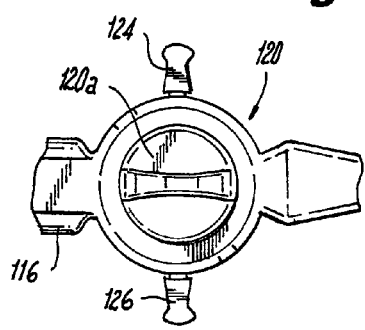
Fig. 1B
Fig. 1C
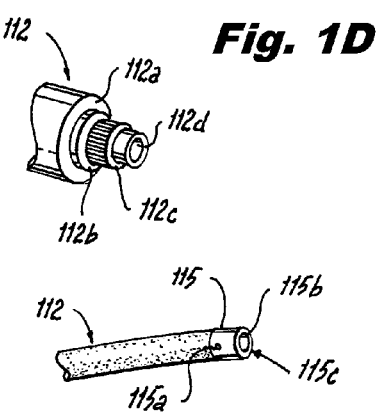
Fig. 1D
Fig. 1E

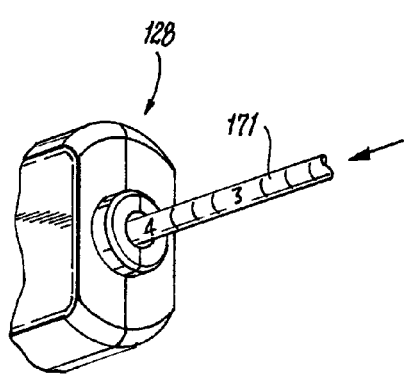
Fig. 1F
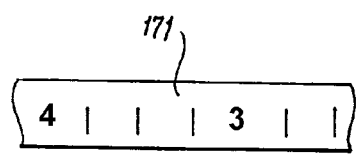
Fig. 1I
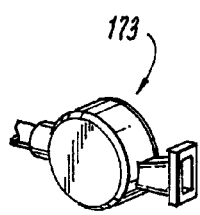
Fig. 1H
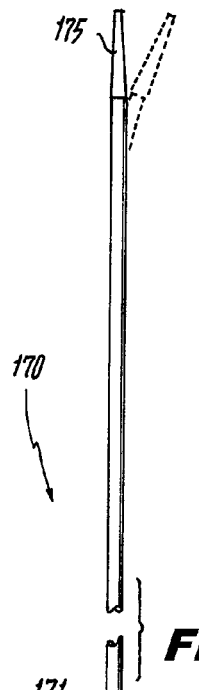
Fig. 1G
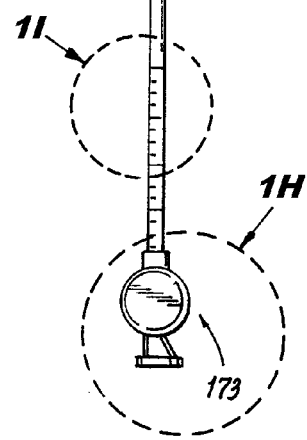

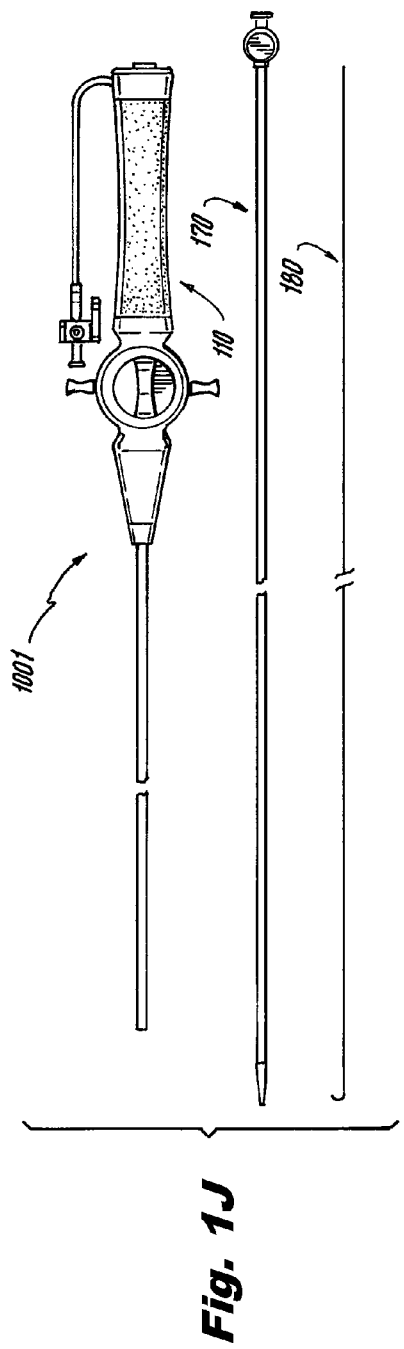
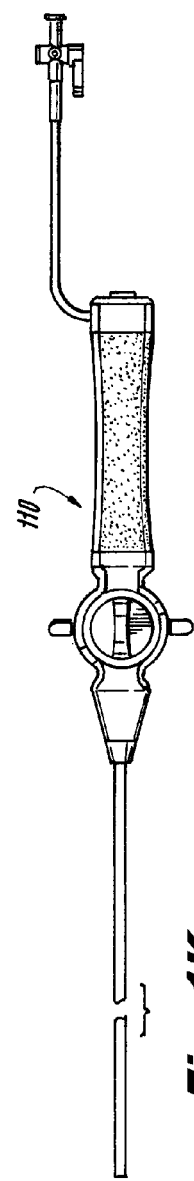
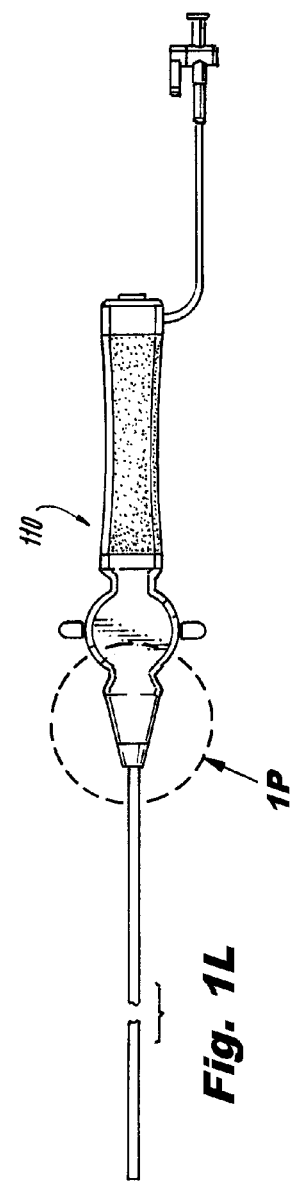
Fig. 1J
Fig. 1K
Fig. 1L

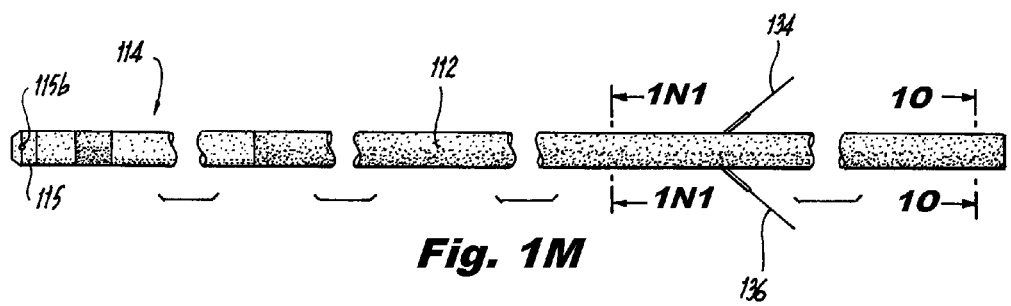
Fig. 1M
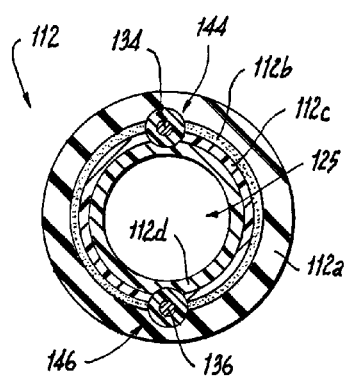
Fig. 1N1
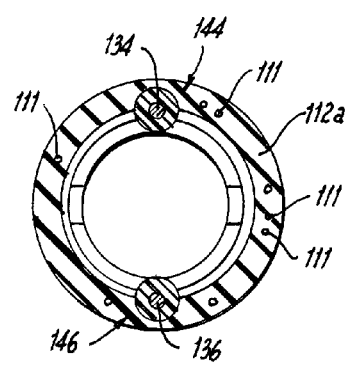
Fig. 1N2
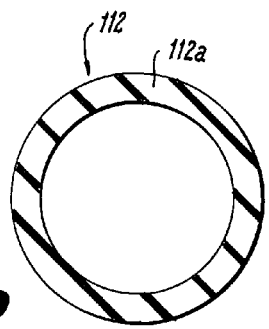
Fig. 1O
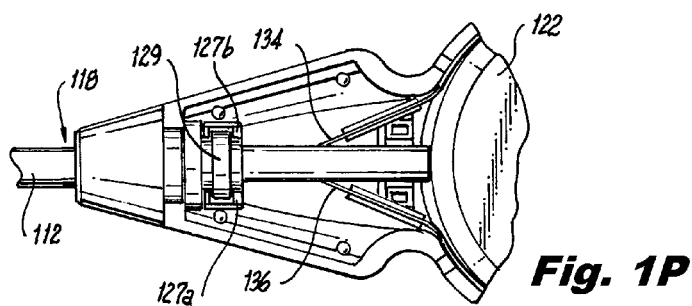
Fig. 1P

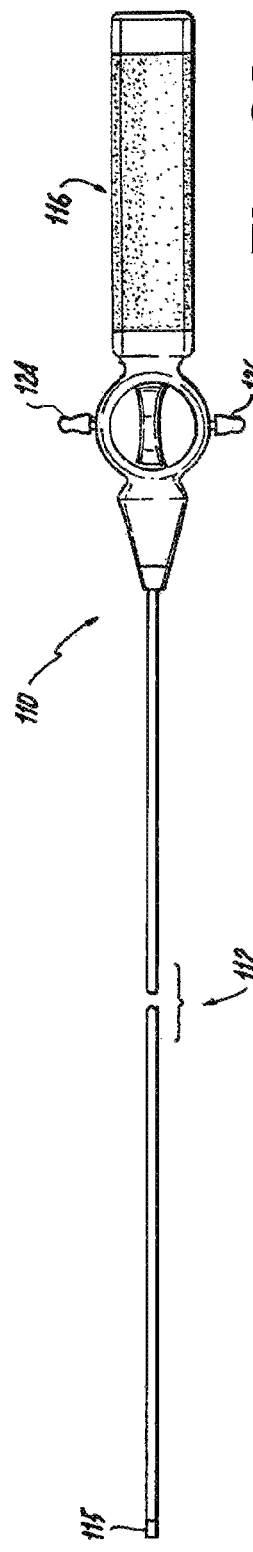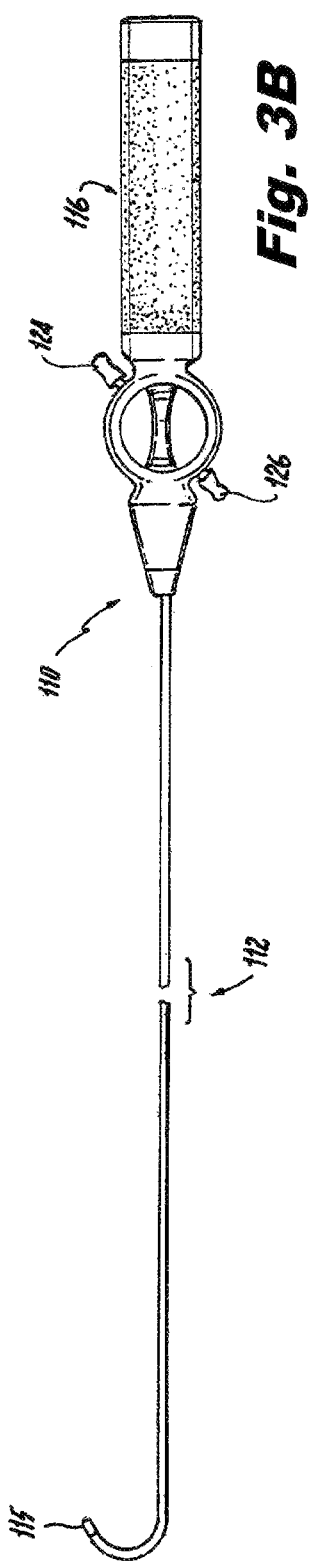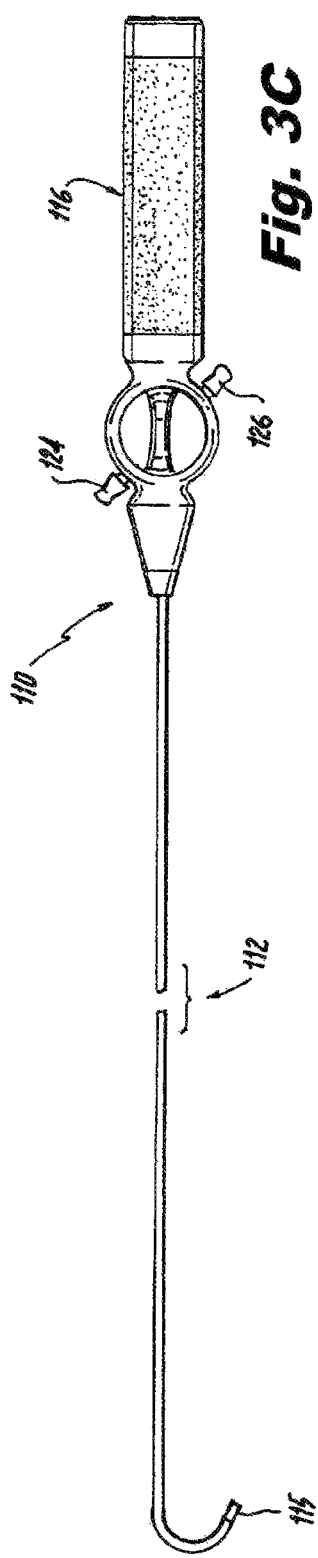

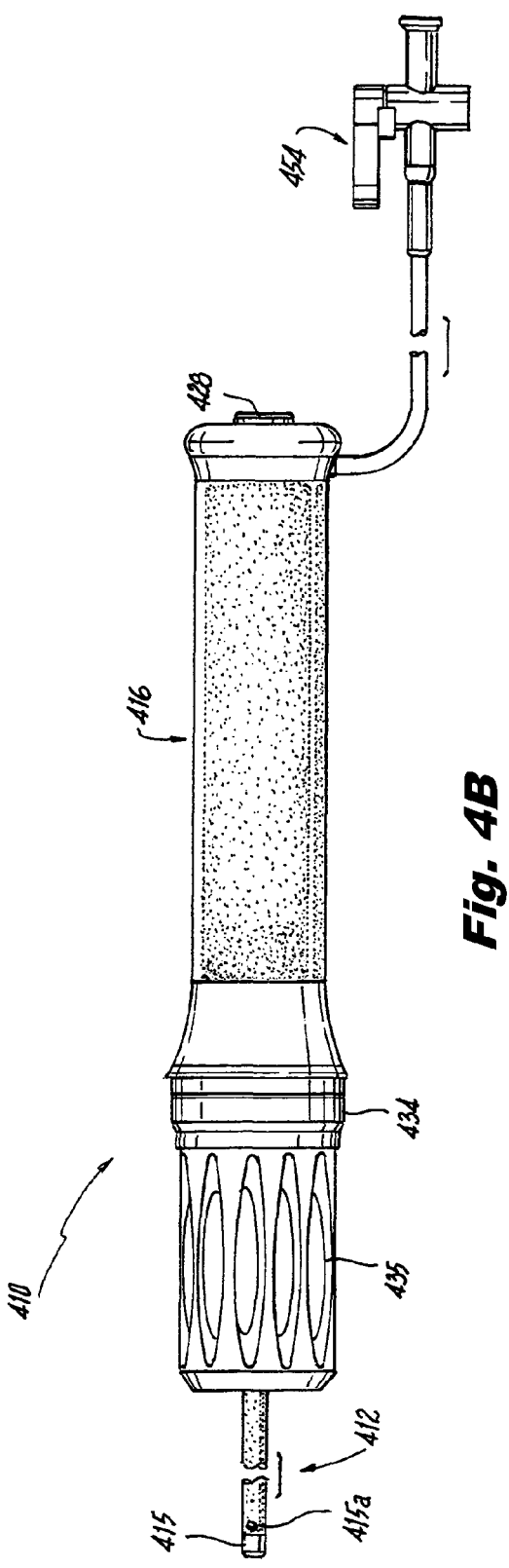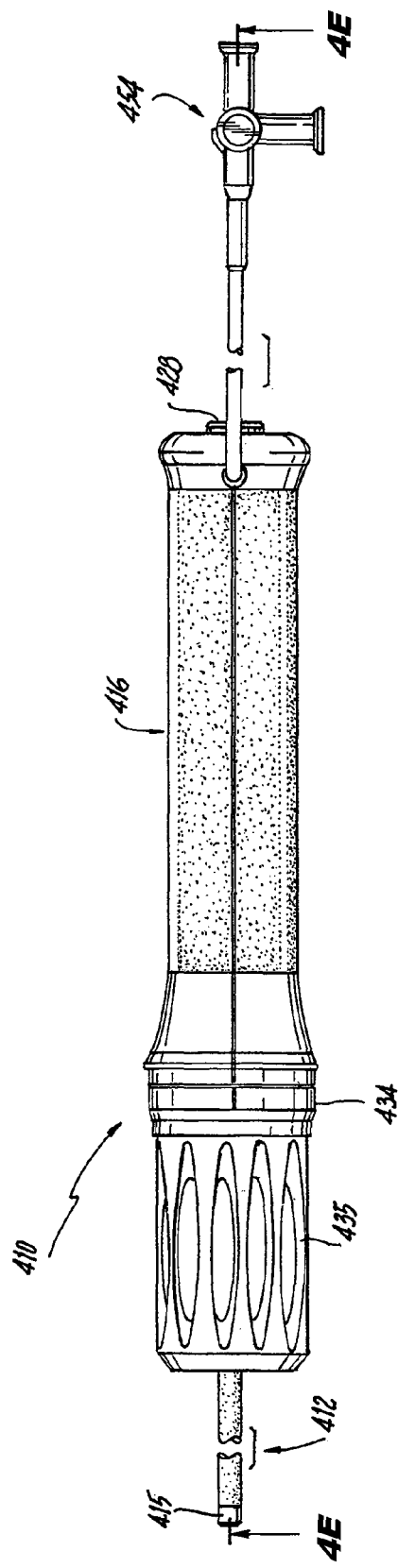
Fig. 4B
Fig. 4C

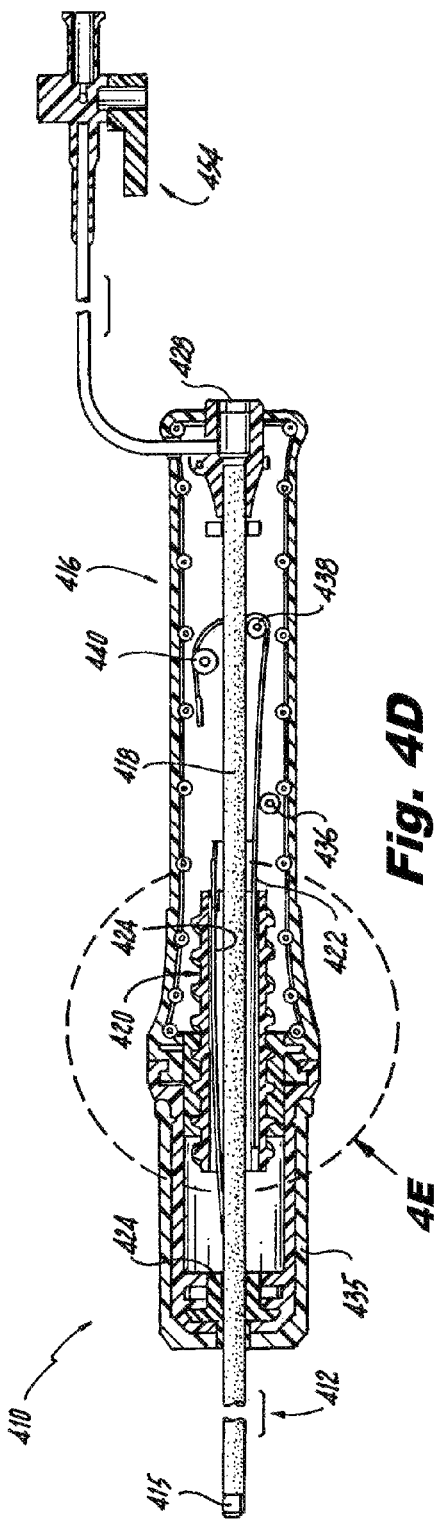
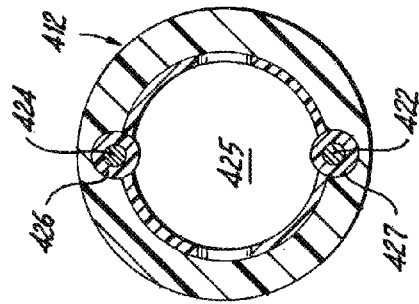
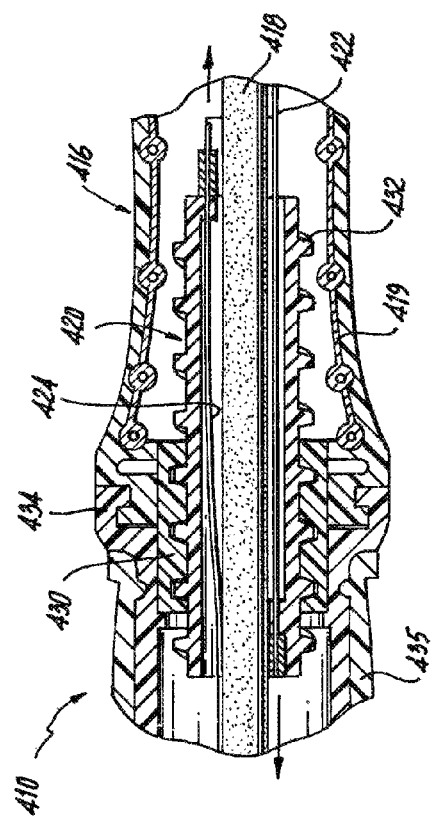
Fig. 4D
Fig. 4F
Fig. 4E

STEERABLE MEDICAL DEVICES

CROSS-REFERENCE TO RELATED APPLICATIONS

This application claims the benefit of and priority to U.S. Provisional Application No. 61/869,140, filed Aug. 23, 2013, and U.S. Provisional Application No. 61/886,132, filed Oct. 3, 2013, the contents of each being incorporated by reference herein in their entirety.

BACKGROUND OF THE INVENTION

1. Field of the Invention

The subject invention is directed to steerable medical devices such as guiding sheaths and handles therefor, which are adapted and configured for the introduction and placement of diagnostic and therapeutic devices into the human vasculature.

2. Description of Related Art

There are many instances where physicians must introduce diagnostic and therapeutic devices such as diagnostic and therapeutic electrodes, ultrasound transducers, biopsy devices and other surgical tools into the body. The diagnostic and therapeutic devices are often carried by catheters which allow physicians to gain access to the body in a minimally invasive manner by way of bodily lumens. In cardiac treatment, for example, a catheter is advanced through a main vein or artery into the region of the heart that is to be treated.

Guiding catheters and sheaths are commonly used to introduce balloon catheters and stents into the vascular system (e.g., for percutaneous transvascular coronary angioplasty), to introduce cardiac pacing leads into the coronary sinus (e.g., for left ventricular pacing and cardiac resynchronization procedures), or to introduce radiofrequency ablation catheters into the left atrium (e.g., for treatment of atrial fibrillation) or into the renal artery for renal denervation procedures.

Guiding catheters and sheaths typically come in French sizes ranging from 4 F all the way to 12 F, in some cases even 18 F. Some examples feature an inner lumen extending from the proximal portion all the way to the distal tip section. The inner lumen often has a PTFE liner to make the insertion of a device therethrough as easy and as smooth as possible.

One method of introducing diagnostic and therapeutic apparatus into the body is to introduce a tubular member (typically a "sheath") into the vicinity of the targeted region. A diagnostic or therapeutic apparatus is then passed through the tubular member to the targeted region. If necessary, the diagnostic or therapeutic apparatus may be removed after its function is performed, but the tubular member can be left in place, so that other apparatuses may be advanced to the targeted region to complete the diagnostic and/or therapeutic procedure.

Precise placement of the diagnostic or therapeutic apparatus is very important, especially in those procedures concerning the heart. To that end, some conventional sheaths are guided to the targeted region with a steerable catheter that is located within the sheath lumen. Once the sheath reaches the targeted region, the steerable catheter is removed from the sheath and a catheter carrying the diagnostic or therapeutic apparatus is advanced through the lumen. This type of sheath lacks any onboard steering mechanism. As a result, redeployment of the distal portion of sheath, even to a region in close proximity to the initially targeted region, requires the withdrawal of the diagnostic or therapeutic apparatus and the reintroduction of the steering catheter.

Other conventional sheaths include a steering mechanism that allows the physician to deflect the distal portion of the sheath. The steering mechanism consists primarily of one or more steering wires. One end of each steering wire is secured to the distal end of the sheath, while the other end is secured to a steering control device, such as the rotating cam and steering control knob arrangement commonly found in steerable catheters.

A major shortcoming of currently manufactured steerable guiding sheaths is that the steering mechanism and or the deflection of the distal sheath section is not precise enough, and or might require different steering precision and/or maximum steering angle for different applications and intended uses. For example, to deliver a larger ablation catheter into the left atrium to treat atrial fibrillation, it might require a steerable guiding sheath with a 1:1 gear ratio to achieve tip deflection of up to 270 degrees in both directions, while the delivery of an ablation catheter through the sheath into the renal artery might require a very precise deflection control and a gear ratio of 3:1 with a deflection of only 90 degrees in both directions. Also it takes more force to deflect a 14 F guiding sheath or catheter as compared to a 6 F guiding sheath or catheter.

There is therefore a need in the art for improved steerable guiding sheaths, catheters, dilators, and handle assemblies which provide relatively precise directional steering and versatility.

SUMMARY

In at least one aspect of this disclosure, a steerable medical device includes a sheath defining a longitudinal axis having a deflectable distal end portion, and at least one lateral passage extending therethrough and configured to accommodate at least one steering cable and a steering handle operatively associated with a proximal end portion of the sheath and having an actuation mechanism operatively connected to the at least one steering cable accommodated within the at least one lateral passages of the sheath for steering the deflectable distal end portion of the sheath in at least one direction relative to the longitudinal axis thereof.

The at least one lateral passage can include two diametrically opposed lateral passages and the at least one steering cable includes two steering cables, one associated with each lateral passage.

The sheath can include a central lumen extending therethrough. A hemostatic seal can be operatively associated with the proximal end portion of the sheath such that the hemostatic seal is in fluid communication with the central lumen.

The central lumen of the sheath can be configured to receive at least one medical device therethrough. The sheath can include an outer diameter size ranging from about 4 F to about 18 F. The proximal end portion of the sheath can extend through the steering handle to a proximal end thereof.

The sheath can include a tubular section reinforced with at least one of braiding, mesh, or wires or any other suitable design. The steerable device can further include a flexible dilator dimensioned for introduction through the central lumen of the sheath and having an axial passage extending therethrough for accommodating a flexible guide wire.

The steerable device can further include a flexible guide wire for introduction through the axial passage of the flexible dilator. The dilator can include depth markings disposed along a length of the dilator for indicating how deep the dilator is inserted into the central lumen of the sheath.

In some embodiments, the sheath can include a hydrophobic coating on an exterior surface thereof. The sheath can include a soft atraumatic tip portion disposed at the distal end portion. The distal end portion of the sheath can include a radiopaque marker band for determining the location of the distal end of the sheath in situ.

An infusion port can be operatively associated with the proximal end portion of the sheath. The distal end portion of the sheath can include at least two side holes in fluid communication with the infusion port for introducing fluid through the distal end portion of the sheath.

In at least one aspect of this disclosure, a steering handle for a steerable medical device for effectuating bi-directional steering of the sheath can include an actuation mechanism operatively connectable to at least one steering cable of the steerable medical device, wherein the actuation mechanism includes a drive nut threadably coupled to a worm coil such that rotation of the drive nut causes axial translation of the worm coil within the steering handle.

The actuation mechanism can include a torque ring operatively associated with the drive nut and configured to rotate about a longitudinal axis of the handle in two directions to bi-directionally steer the sheath. The torque ring can be manually operable. At least one steering wire can be operatively connected to a distal end portion of the worm coil and another steering wire is connected to a proximal end portion of the worm coil.

The steering wire connected to the distal end portion of the worm coil is longer than the steering wire connected to the proximal end portion of the worm coil. The longer steering wire is looped around a spring biased guide roller within the handle assembly. The worm coil has a constant thread pitch selected to achieve a desired degree of bidirectional deflection of the distal end portion of the sheath.

In at least one aspect of this disclosure, a steering handle for a steerable medical device configured for effectuating bi-directional steering of the sheath can include an actuation mechanism operatively connectable to at least one steering cable of the steerable medical device, wherein the actuation mechanism includes diametrically opposed actuators extending from a central hub operatively connectable to the two or more steering wires.

The handle can further include a locking mechanism configured to provide a resistance to turning the actuators. The locking mechanism can provide a resistance to the central hub via a locking member that is cammed against an inner surface of the handle.

In at least one aspect of this disclosure, a kit for placing a surgical device in the vasculature of patient, comprising an enclosure and a steerable medical device as disclosed herein. The kit can further include a dilator disposed within the enclosure configured to be inserted into the sheath. The kit can further include a guide wire disposed within the enclosure.

BRIEF DESCRIPTION OF THE DRAWINGS

So that those skilled in the art to which the subject invention appertains will readily understand how to make and use the subject invention without undue experimentation, reference may be had to the figures, wherein:

FIG. 1A is an illustration of an embodiment of a bi-directional steerable guiding sheath in accordance with this disclosure, adapted for the introduction and placement of diagnostic and therapeutic devices into the human vasculature, e.g., intracardiac and transseptal placement;

FIG. 1B is an enlarged illustration of a lockable actuation mechanism disposed on the handle portion of the sheath of FIG. 1A;

FIG. 1C is an illustration of a section of the sheath of FIG. 1A, showing the outer surface of the sheath including a hydrophobic coating;

FIG. 1D is an illustration of a cross-section of the sheath of FIG. 1A, showing a braided interior shaft portion of the sheath;

FIG. 1E is an illustration of an embodiment of a soft atraumatic tip portion of the sheath of FIG. 1A, shown including two side holes for irrigation;

FIG. 1F is an illustration of an embodiment of a hemostatic seal at the proximal end of the ergonomic handle assembly of the steerable guiding sheath shown in FIG. 1A;

FIG. 1G is an illustration of an embodiment of a flexible dilator that can be used in conjunction with the steerable guiding sheath of FIG. 1A;

FIG. 1H is an illustration of an embodiment of a French size and guide wire indicator on the proximal end of the dilator of FIG. 1G;

FIG. 1I is an illustration of depth markings presented on the dilator of FIG. 1G;

FIG. 1J is an illustration of an embodiment of a kit containing the steerable guiding sheath of FIG. 1A, the dilator of FIG. 1G, and a guide wire;

FIG. 1K is a top plan view of the steerable guide sheath of FIG. 1A, shown including an infusion port and associated tubing;

FIG. 1L is a bottom plan view of the steerable guide sheath of FIG. 1A;

FIG. 1M is a side elevational view of the sheath of FIG. 1A, with the steering wires shown entering a proximal portion thereof;

FIG. 1N1 is a cross-sectional view of an embodiment of the sheath shown in FIG. 1M taken along line 1N1-1N1;

FIG. 1N2 is a cross-sectional view of another embodiment of the sheath shown in FIG. 1M taken along line 1N1-1N1, showing including reinforcing wires disposed within the outer sheath;

FIG. 1O is a cross-sectional view of the sheath shown in FIG. 1M taken along line 1O-1O;

FIG. 1P is a cross-sectional view of the handle portion of the steerable guide sheath, with reference to FIG. 1L;

FIG. 3A is a depiction of the bi-directional steerable guiding sheath of FIG. 1A shown having the distal end portion of the dilator body in a straight condition;

FIG. 3B is a depiction of the bi-directional steerable guiding sheath of FIG. 3A shown having the distal end portion of the dilator body in a first deflected position;

FIG. 3C is a depiction of the bi-directional steerable guiding sheath of FIG. 3A shown having the distal end portion of the dilator body in a second deflected position;

FIGS. 4B-4D illustrate aspects of the handle assembly of the steerable guiding sheath of FIG. 4A;

FIG. 4E is an enlarged partial cross-sectional view of the handle assembly shown in FIG. 4D, illustrating the internal components of the actuation assembly that activates the two steering wires which control the bi-directional movement of the distal end portion of the sheath;

FIG. 4F is a cross-sectional view of the sheath of FIG. 4A, illustrating the central lumen and opposed passages that accommodate the two steering wires.

ENABLING DESCRIPTION OF THE INVENTION

Figure 1Q:
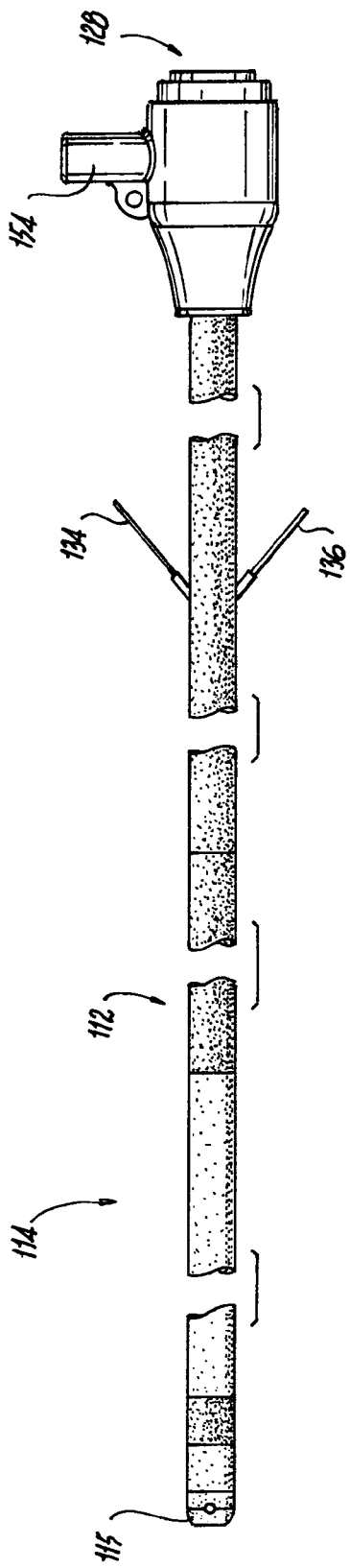
FIG. 1Q is a side, elevational view of the sheath of FIG. 1A, shown with an embodiment of an over molded hub that supports a hemostatic seal, e.g., as shown in FIG. 1F.
Figure 1R:
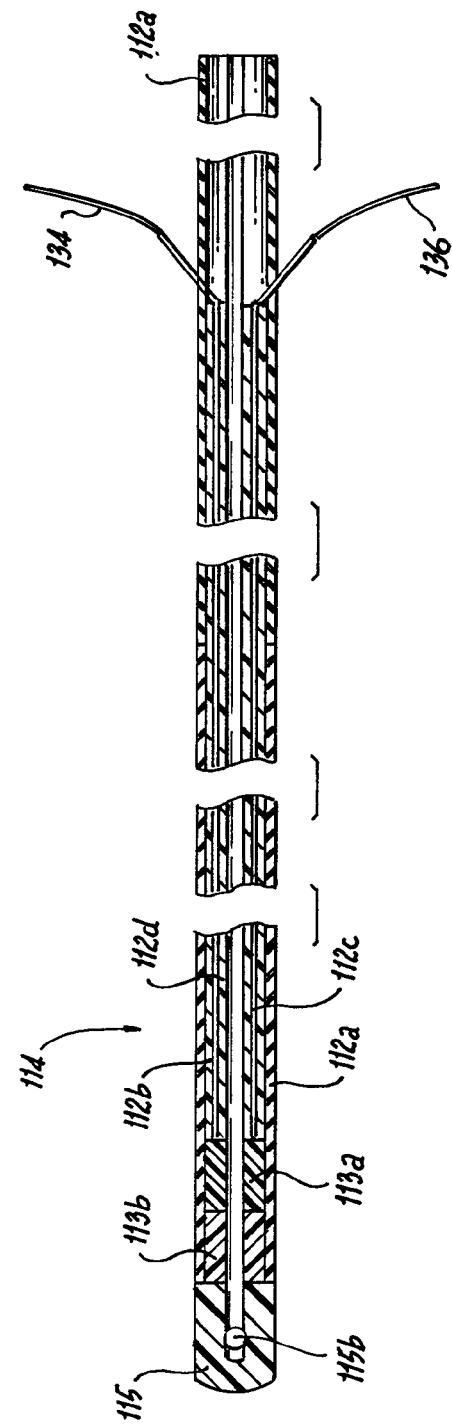
FIG. 1R is a longitudinal cross-sectional view of the sheath of FIG. 1Q, illustrating the various internal structures and steering wires.

Referring now to the drawings wherein like reference numerals identify similar structural features or elements of the disclosed devices, embodiments of this disclosure are directed to guiding catheters including a sheath and handle assemblies for steering said sheaths.

In at least one aspect of this disclosure, referring generally to FIGS. 1A-2N, the steerable guiding sheath 110 can include an elongated sheath 112 having a deflectable distal end portion 114. The sheath 112 can include and/or define a central lumen 125 and a pair of diametrically opposed lateral passages 144, 146 to accommodate a corresponding pair of steering cables 134, 136. While the embodiment of FIG. 1A is shown as having two lateral passages 144, 146 and two steering cables 134, 136, any suitable number of passages and/or cables are contemplated herein, e.g., one, two, three, four, or more.

The sheath 112 can have any suitable outer diameter size for a desired use. In some embodiments, the outer diameter size of the sheath 112 ranges from about 4 F to about 18 F. In some embodiments, the outer diameter of the sheath 112 is about 5 F.

The proximal end portion 118 of the sheath 112 can extend through the steering handle 116 to a proximal end thereof. A hemostatic seal 128 can be operatively associated with the proximal end portion 118 of the sheath 112 such that the hemostatic seal 128 is in fluid communication with the central lumen 125 thereof. In at least some embodiments, the hemostatic seal 128 can provide an effective seal for a guide wire of about 0.014 inches.

The sheath 112 can have a hydrophobic coating or any other suitable and/or desired coating. In some embodiments, the sheath 112 can be formed from a hydrophobic material.

The sheath 112 can include a multi-layer structure at one or more portions thereof. Referring to FIGS. 1D and 1N1, a portion of the sheath 112 can include one or more of an outer layer 112a, a secondary layer 112b, a braided layer 112c, and/or an internal layer forming a central lumen 112d. The outer layer 112a, the secondary layer 112b, and the internal layer 112d can include any suitable flexible material, e.g., a biocompatible plastic, metal, or the like. The braided layer 112c can include any suitable braided structure made up of strands of any suitable material (e.g., biocompatible plastic, fabric, metal). In some embodiments, the braided layer 112 is formed into the one or more of the outer layer 112a and/or the secondary layer 112b such that the outer layer 112a and/or secondary layer 112b have braiding or mesh included therein (e.g., via over molding biocompatible plastic on a braided/mesh tubing).

Alternatively, referring to FIG. 1N2, the sheath 112 can include reinforcing wires 111 disposed within the outer sheath 112a. The reinforcing wires 111 can be made of any suitable material (e.g., metal) and may be configured for a specific rigidity. The reinforcing wires 111 may be configured as a mesh layer molded into the outer layer 112a.

Using such designs as shown in FIGS. 1N1 and 1N2 can allow the flexibility of sheath 112 to be controlled. In some embodiments, the flexibility of the sheath 112 can be modified as a function of length of the sheath 112 to control the point along the sheath 112 that the distal portion deflects about and/or degrees of deflection of portions of the sheath 112.

As shown in FIG. 1O, such a multi-layer structure may comprise only a portion of the sheath 112, and another portion of the sheath 112 (e.g., a proximal portion within the handle) can include only an outer layer 112a. Any other suitable configuration for sheath layering or sheath design is contemplated herein.

Referring specifically to FIGS. 1A, 1M, 1Q, and 1R, the sheath 112 can also include a soft atraumatic tip portion 115 disposed on the distal end thereof. In some embodiments, the tip portion 115 can include one or more side holes 115a, 115b in fluid communication with an infusion port 154 (e.g., including a conventional leur fitting) associated with the steering handle 116. As shown in FIG. 1E, the tip portion 115 can include an opening 115c in fluid communication with the central lumen 125.

The distal end portion 114 can also include a radiopaque marker 113b. The radiopaque marker 113b can be any suitable shape (e.g., a cylinder) and can include any radiopaque material and/or the like for locating the radiopaque marker 113b in situ to enable the visual guidance of the sheath 110 through the vascular system of a patient using a suitable imaging system.

The distal end portion 114 can also include and anchor member 113a disposed therein configured to anchor the steering wires 134, 136 to the distal end portion 114. The anchor member 113a can be of any suitable shape (e.g., cylindrical) and mounted within the distal end portion 114 of the sheath 112 such that the anchor member 113a does not move relative to the distal tip when pulled on by the steering wires 134, 136.

The steerable guiding sheath 110 further includes a steering handle 116 operatively associated with a proximal end portion 118 of the sheath 112 and an actuation mechanism 120 that is operatively connected to the pair of steering cables 134, 136 accommodated within the opposed lateral passages 144, 146 of the sheath 112 for steering the deflectable distal end portion 114 of the sheath 112 in one or more directions (e.g., bi-directionally as shown in this embodiment).

Figure 2A:
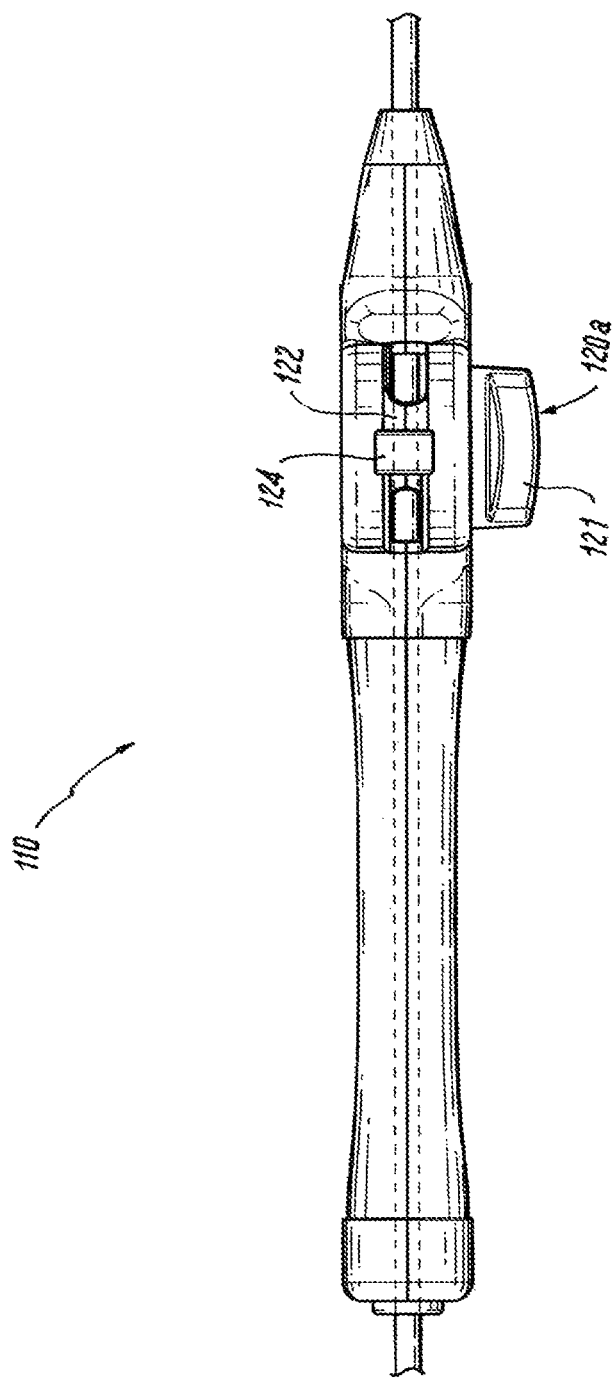
FIG. 2A is a side elevational view of the handle of the steerable guiding sheath of FIG. 1A.
Figure 2B:
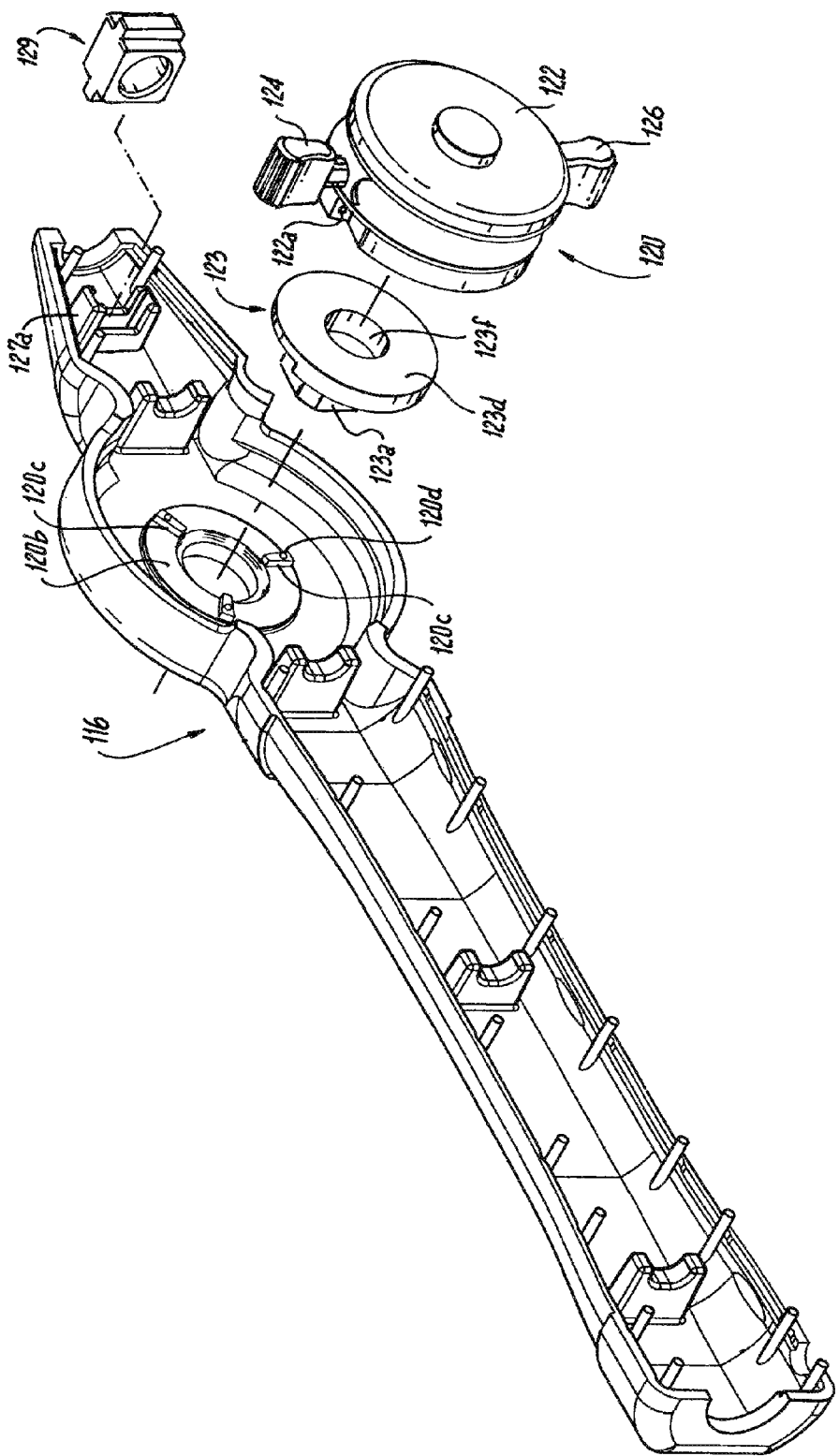
FIG. 2B is a perspective exploded view of a first half of the handle of FIG. 2A showing an actuation mechanism and other internal components relative to a first half of the handle housing.
Figure 2C:
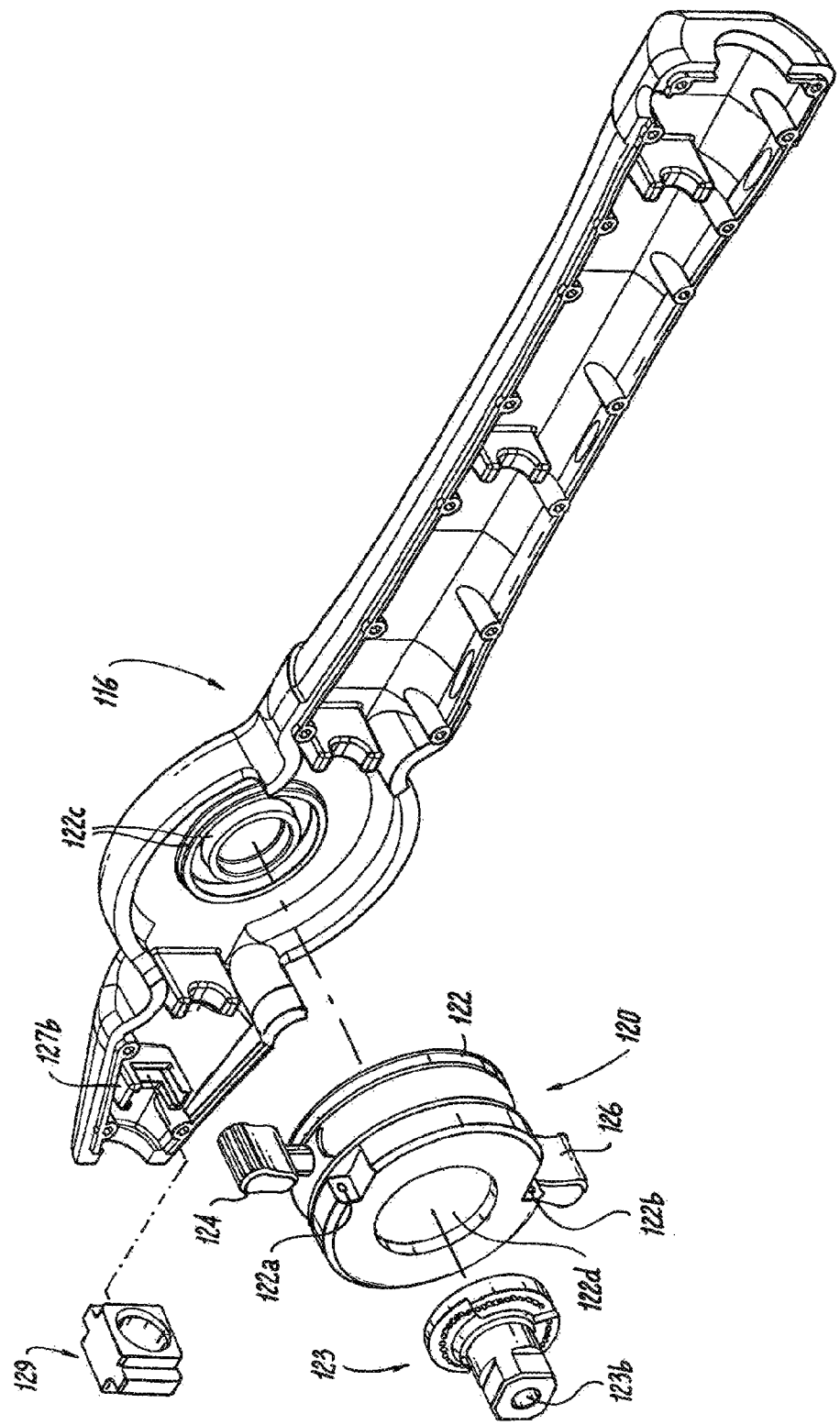
FIG. 2C is a perspective exploded view of a second half of the handle of FIG. 2A showing an actuation mechanism and other internal components relative to a second half of the handle housing.
Figure 2D:
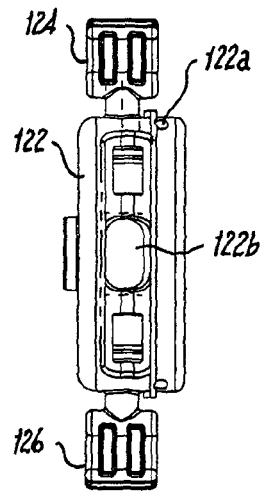
FIG. 2D is a front view of the actuation mechanism of FIGS. 2B and 2C.
Figure 2E:
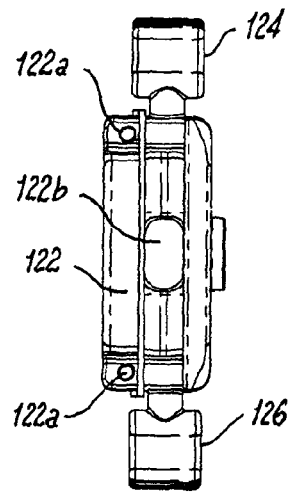
FIG. 2E is a rear view of the actuation mechanism of FIGS. 2B and 2C.
Figure 2F:
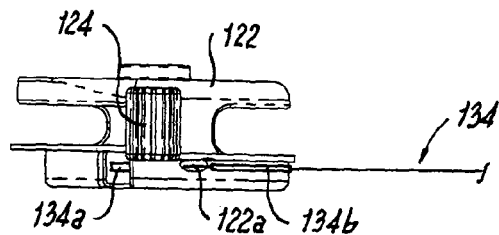
FIG. 2F is a side view of the actuation mechanism of FIGS. 2B and 2C.

Referring to FIG. 2A-2C, a first half 116a of the handle 116 includes lock surface 120b on the inside portion of the first half 116a defining an opening between the inside of the handle 116 and the outside thereof. The lock surface 120b includes one or more cam protrusions 120c extending from the lock surface 120b. The cam protrusions 120c include one or more lock protrusion 120d. The cam protrusions 120c are configured to engage a friction lock member 123 described in more detail below.

As shown in FIGS. 2B and 2C, the first and second halves 116a, 116b are dimensioned to accept the actuation mechanism 120 therein. As shown in FIG. 2C, the second half 116b can include ridges 122c or any other surface inside the second half 116b to allow the central hub 122 of the actuation mechanism 120 to rotate relative to the handle 116.

Referring to FIGS. 2B, 2C, and 2D-2F, the actuation mechanism 120 of the steering handle 116 can include a central hub 122 connected to the actuators 124, 126. The central hub 122 can define a passageway 122b configured to allow the sheath 112 to pass therethrough. The passageway 122b is dimensioned to prevent bending or moving the portion of the sheath 112 passing therethrough between the limits of actuation of the actuation mechanism 120.

The flexible steering cables 134, 136 can be secured to the periphery of the central hub 122 of actuation mechanism 120. For example, the central hub 122 can define wire holes 122a which steering cables 134, 136 can pass through. The steering cables 134, 136 can be secured to the central hub 122 using a crimp 134a or any other suitable attachment. In some embodiments, a guide member 134b can be disposed around the steering cable 134, 136 distal of the wire holes 122a to prevent the steering cables from bending around the central hub 122 allowing the steering cables 134, 136 to angle inwardly toward the sheath 112 without bending the cables 134, 136.

Also as shown best in FIG. 2C, the central hub 122 can define a friction lock cavity 122d configured to accept a friction lock member 123 therein. As shown the actuation mechanism 120 can be a single molded piece of material (e.g., suitable plastic), but any suitable combination of parts is contemplated herein.

As shown in FIG. 2B, a friction lock member 123 is configured to be disposed between the actuation mechanism 120 and the first half 116a of the housing 116. Referring to FIG. 2I-2L, the friction lock member 123 can include a pedestal portion 123a defining a hole 123b therethrough and a flange portion 123d extending from the pedestal portion 123a. The flange portion 123d can define a frictional surface for engaging the central hub 122 of the actuation mechanism 120. In addition, the flange portion 123d includes one or more camming surfaces 123c which can define locking divots 123e. The camming surfaces 123c can include any suitable shape (e.g., ramped as shown).

Figure 2G:
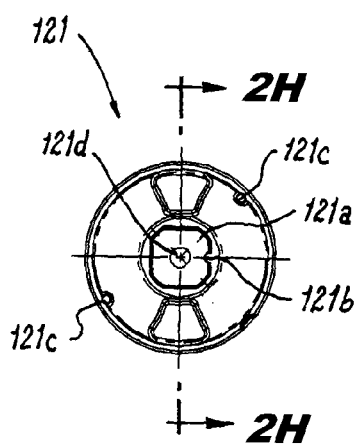
FIG. 2G is a bottom plan view of a locking tab of the locking mechanism of the device of FIG. 2A.
Figure 2H:
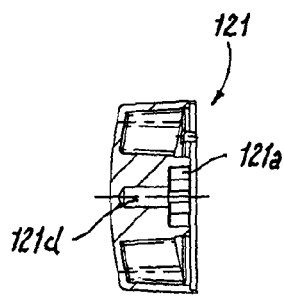
FIG. 2H is a cross-sectional side view of a locking tab of the locking mechanism of the device of FIG. 2A.
Figure 2I:
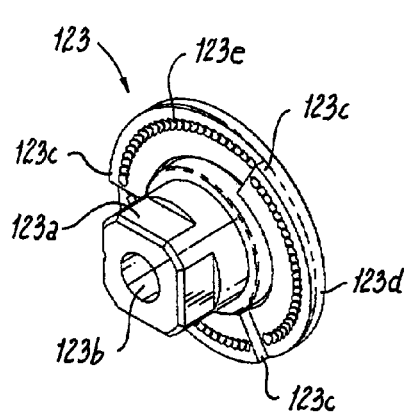
FIG. 2I is a perspective view of an embodiment of the friction lock member of FIGS. 2B and 2C, showing camming surfaces and locking divots on the camming surfaces.
Figure 2J:
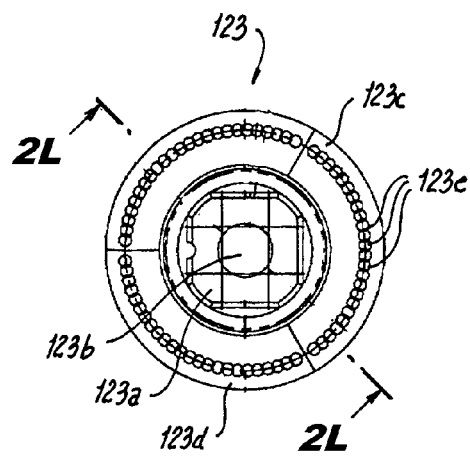
FIG. 2J is a top plan view of an embodiment of the friction lock member of FIG. 2I.
Figure 2K:
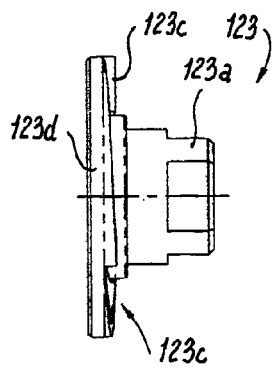
FIG. 2K is a side view of an embodiment of the friction lock member of FIG. 2I.

Referring to FIGS. 2G and 2H, a locking tab 121 of the locking mechanism 120a can include a body 121b shaped to be gripped by a user and a pedestal cavity 121a defined therein dimensioned to receive the pedestal portion 123a of the friction lock member 123. An attachment hole 121d can be included within the pedestal cavity 121a to allow a screw or other suitable member to affix thereto to attach the friction lock member 123 to the locking tab 121.

Figure 2L:
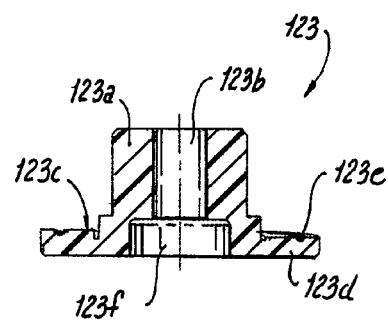
FIG. 2L is a cross-sectional side view of an embodiment of the friction lock member of FIG. 2I.

Referring additionally to FIG. 2L, an attachment member (e.g., a screw) can be passed through hole 123b and into attachment hole 121d to attach the friction lock member 123 to the locking tab 121 in a sandwich with the housing 116 therebetween. The attachment member can be dimensioned such that a head of the attachment member can seat into head cavity 123f of the and an attachment portion of the attachment member can advance into attachment hole 121d sufficiently to sufficiently sandwich the housing 116 between the locking tab 121 and the friction lock member 123 against the lock surface 120b while still allowing the assembly to rotate when the locking tab 121 is rotated.

In this regard, the cam protrusions 120c maintain contact with the camming surfaces 123c such that when the locking tab 121 is rotated, the friction lock member 123 rotates therewith causing the relative position of the cam protrusions 120c to change relative to the camming surfaces 123c. When the cam protrusions 120c are in contact with a thicker portion of the camming surfaces 123c, the friction lock mechanism 123 is moved closer to the central hub 122, causing the friction surface of the flange 123d to push upon the central hub 122 to produce more frictional resistance to rotation of the hub 122. The lock protrusions 120d mate with the locking divots 123e to prevent the locking member 123 from slipping back down the cam path and provide a tactile feedback while turning the locking tab 120a between an unlocked position and a locked position.

Any other suitable locking mechanism 120a and/or components thereof to prevent or inhibit movement of the actuators 124, 126 is contemplated herein.

Figure 2M:
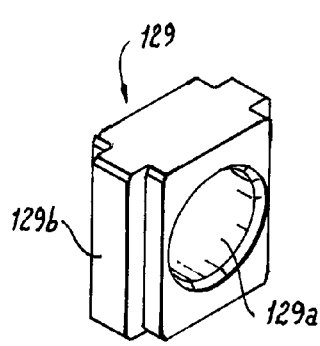
FIG. 2M is a perspective view of a sheath stabilizing member, showing a sheath hole and flange members extending therefrom.
Figure 2N:
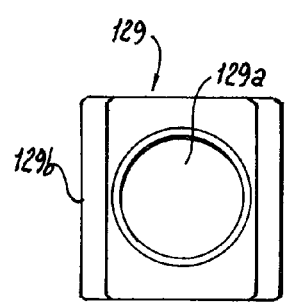
FIG. 2N is a top plan view of the sheath stabilizing member of FIG. 2M.

Referring to FIGS. 2M and 2N in conjunction with FIGS. 2B and 2C, a sheath stabilizing member 129 can include a sheath hole 129a dimensioned for the sheath to pass therethrough and flange members 129b extending therefrom. The sheath stabilizing member 129 is configured to fit within stabilizing member holders 127a, 127b that are disposed on the inside of the first and second halves 116a, 116b, respectively. The sheath stabilizing member 129 allows the sheath 112 to be directed at the distal end of the handle 116 so that motion of the sheath 112 within the handle 116 can be resisted.

When assembled and in an unlocked position, the actuation mechanism 120 can rotate between first half 116a and second half 116b of the housing 116 to steer the distal tip of the sheath 112. The locking tab 121 can be moved between an unlocked position such that the actuation mechanism 120 can rotate without substantial resistance and a locked position such that a resistance to rotation is created by the locking mechanism 120a.

Additionally, positions between the unlocked and locked position can be selected by a user such that the sensitivity of control of the distal end of the sheath 112 is modified. In such an instance, the amount of force provided by the locking mechanism 120a can be modified by turning the locking mechanism 120a to a particular position between the locked position and the unlocked position, thereby altering the force required to deflect the distal end portion 114. This can be used to allow the user to modify the sensitivity of the actuating mechanism 120 using the locking mechanism 120a.

Referring to FIGS. 3A-3C the sheath 112 is shown being steered from a straight position (FIG. 3A) to a first deflected position (FIG. 3B) and a second deflected position (FIG. 3C). In use, manipulation of the actuators 124 and 126 in clockwise and counter-clockwise directions causes the corresponding movement of the central hub and steering cables 134 and 136. This results in the bi-directional deflection of the distal end portion 114 of the sheath 112. It is contemplated that clockwise actuator motion can lead to a counter-clockwise tip deflection, and vice versa. The actuation mechanism 120 controls the orientation of the distal end portion of the sheath and can be designed to have any suitable maneuverability (e.g., 180° dual deflection maneuverability).

Referring to FIGS. 1F-1J, the steerable guiding sheath 110 can further include and/or be operative with a flexible dilator 170 dimensioned for introduction through the central lumen 125 of the sheath 112 and/or the hemostatic seal 128. The dilator 170 includes a dilator shaft 171 and a dilator tip 175. In some embodiments, the dilator 170 can have an axial passage extending therethrough for accommodating a flexible guide wire 180. As shown in FIGS. 1F and 1I, in some embodiments, the dilator 170 can further include depth markings for accurate placement and/or indicia indicating French size. Indicia for indicating French size of the dilator shaft 171 can be located on a proximal portion 173 or any other suitable portion of the dilator 170.

Referring specifically to FIG. 1J, a kit 1001 for placing a surgical device in the vasculature of patient can include an enclosure (not shown), a steerable guiding sheath 110 disposed within the enclosure, a dilator 170 disposed within the enclosure, and a guide wire 180 disposed in the enclosure.

In at least one aspect of this disclosure, referring now to FIGS. 4A-4F, the steerable medical device can be a steerable guiding sheath 410 having a differing handle assembly 416 than the above described embodiments. While this embodiment is described as a steerable sheath, it is contemplated that the handle portion 416 can be included on any other suitable steerable medical device (e.g., a dilator, an electro surgical tool).

Figure 4A:
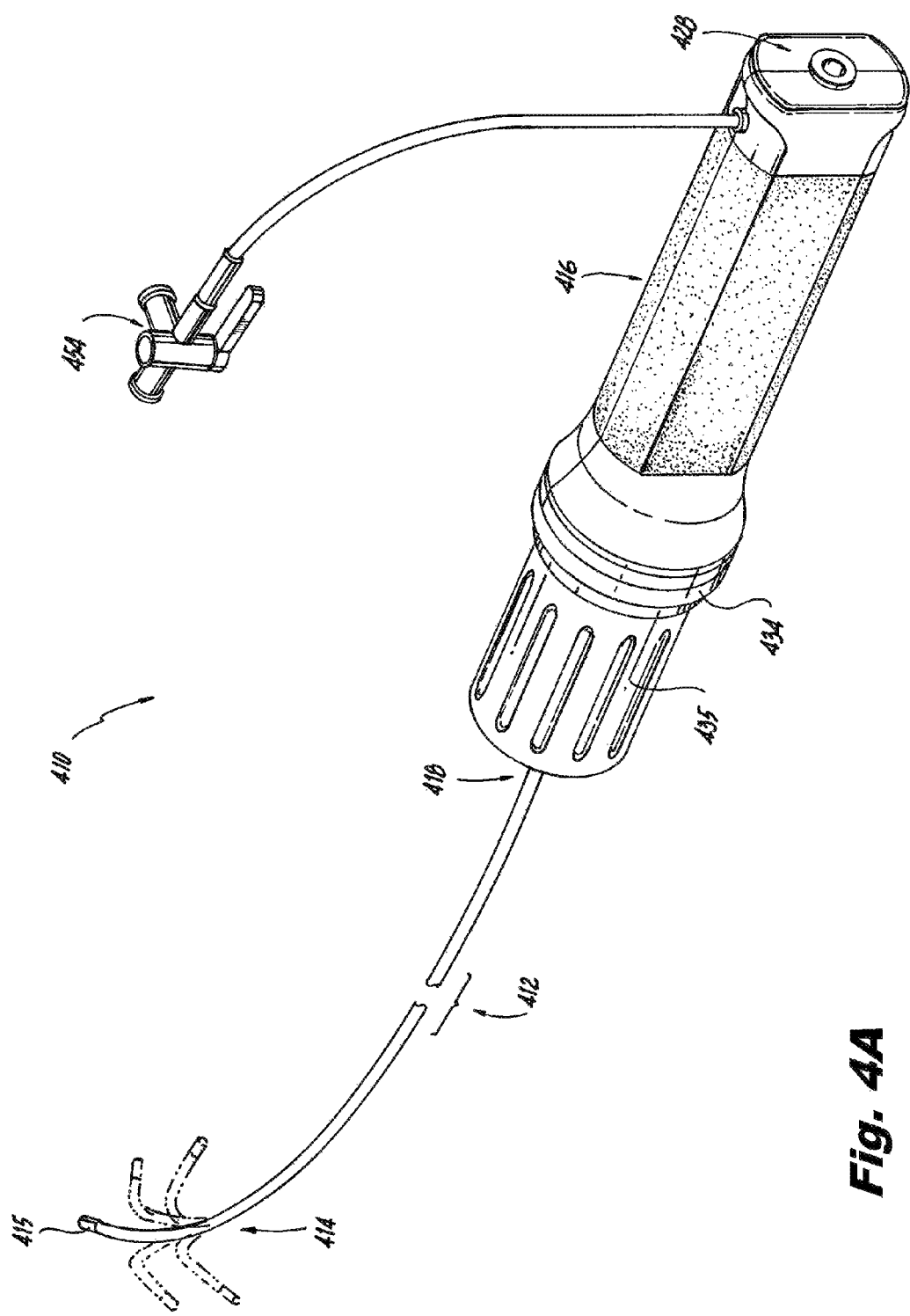
FIG. 4A is an illustration of an embodiment of a bi-directional steerable guiding sheath having another embodiment of a handle assembly in accordance with this present disclosure.

The steerable guiding sheath 410 includes an elongated sheath 412 having a deflectable distal end portion 414 and a central lumen 425 (see FIG. 4F). As shown in FIG. 4A, the distal end portion 414 of sheath 412 can be adapted and configured to achieve about a 180 degree deflection (e.g., mono-directional, bidirectional). Other suitable maximum deflections are contemplated herein.

Similar to the other sheaths described herein, the sheath 412 can have an outer diameter size ranging from about 4 F to about 18 F. Any other suitable size is contemplated herein.

The steerable guiding sheath 410 includes an elongated handle assembly 416 operatively associated with a proximal end portion 418 of the sheath 412. The proximal end portion 418 of the sheath 412 can extend through the steering handle 416 to a proximal end thereof.

A hemostatic seal 428 can be operatively associated with the proximal end portion 418 of the sheath 412 and in fluid communication with the central lumen 425. As disclosed above, a hemostatic seal 428 permits sealed introduction of a dilator, guide wire, or other medical device.

The sheath 412 can include a hydrophobic coating and/or a soft atraumatic tip portion 415 similar to those as described above. The tip portion 415 of the sheath 412 can include a radiopaque marker band similar to marker band 113b as described above. An infusion port 454 (e.g., including a conventional leur fitting) can be operatively associated with the proximal portion of the sheath 412 for fluidly communicating with apertures (not shown) provided in the distal end portion 414 of the elongated sheath 412.

The handle assembly 416 of steerable guiding sheath 410 includes a body 419 that houses a manually operable actuation mechanism 420. The actuation mechanism 420 can be operatively connected to one or more steering wires 422 and 424. As best seen in FIG. 4F, the steering wires 422 and 424 can be accommodated within opposed lateral passages 426 and 427 of the sheath 412. As shown in this embodiment, the steering wires 422 and 424 are arranged to control the deflection of the distal end portion 414 of the sheath 412 in two directions, as described in more detail herein below.

As best seen in FIG. 4E, the actuation mechanism 420 can include a drive nut 430 that is threadably coupled to a worm coil 432. Rotation of the drive nut 430 causes axial translation of the worm coil 432 within the body 419 of the handle assembly 416.

The drive nut 430 and worm coil 432 can include a common thread pitch that is selected to achieve a precise amount of control over the deflection achieved at the distal end portion 414 of the sheath 412. For example, differing thread pitches advance the worm coil 432 at different rates, allowing more or less motion of the tip relative to the amount of motion of the user, thereby modifying precision. It would be appreciated by those having skill in the art that the more control a surgeon has over the deflection of the distal end of the sheath, the easier it is for that surgeon to accurately steer the sheath 412 though the vasculature of a patient to the site of a procedure.

The actuation mechanism 420 further includes a manually rotatable torque ring 434 that is operatively connected to the drive nut 430 and configured to be rotated by a user. The torque ring 434 can be positioned adjacent a stationary torque grip 435, thereby enabling a user to maintain a firm grip on the device 410 while rotating the torque ring 434 to achieve the directional deflection of the distal end portion 414 of the sheath 412.

As shown, the steering wire 422 can be operatively connected or otherwise crimped to a distal end portion of the worm coil 432 of actuation mechanism 420. Also as shown, the other steering wire 424 can be operatively connected or otherwise crimped to a proximal end portion of the worm coil 432. As best seen in FIG. 4D, steering wire 422 can be longer than the steering wire 424.

The longer steering wire 422 can be operatively supported by a pair of guide rollers 436 and 438. Guide roller 436 can be disposed in a stationary position within the body 419 of handle assembly 416. In contrast, guide roller 438 can be dynamically positioned within the body 419 of handle assembly 416, such that the guide roller 438 is operatively associated with a spring biased tension arm 440 that is pivotally mounted within the body 419 of handle assembly 416. As shown in FIG. 4D, the steering wire 422 can be looped around the dynamic guide roller 438 so that it doubles back around toward the crimped end of the wire and then out to the distal end portion 414 of the sheath 412.

In operation, when the worm coil 432 translates in a distal direction through rotation of drive nut 430, the end of the longer steering wire 422 that is crimped to the distal end portion of the worm coil 432 is pulled in a distal direction. Consequently, the portion of steering wire 422 that double backs around guide roller 438 is pulled in a proximal direction. This causes controlled deflection of the distal end portion 414 of the sheath 412.

When the worm coil 432 translates in a proximal direction through the reverse rotation of drive nut 430, the shorter steering wire 424 that is crimped to the proximal end portion of worm coil 432 is pulled in a proximal direction therewith. This causes controlled deflection of the distal end portion 414 of sheath 412 in an opposite direction. At the same time, the crimped end of the longer steering wire 422 moves proximally with the worm coil 432, and the slack in that wire is accommodated by the spring biased tension arm 440.

The actuation mechanism 420 and the arrangement of steering wires 422, 424 allows for the bidirectional deflection of the distal end portion 414 of the sheath 412 using a worm coil 432 that has a single uniform thread pitch. Those skilled in the art will readily appreciate that the amount or degree of deflection, and the associated precision steering that can be achieved, can be adjusted by changing the thread pitch of the drive nut 430 and worm coil 432 as described above. That is, a greater amount of precision for the deflection of the distal end portion 414 of sheath 412 can be achieved by increasing the thread pitch of the drive nut 430 and worm coil 432.

Figure 5:
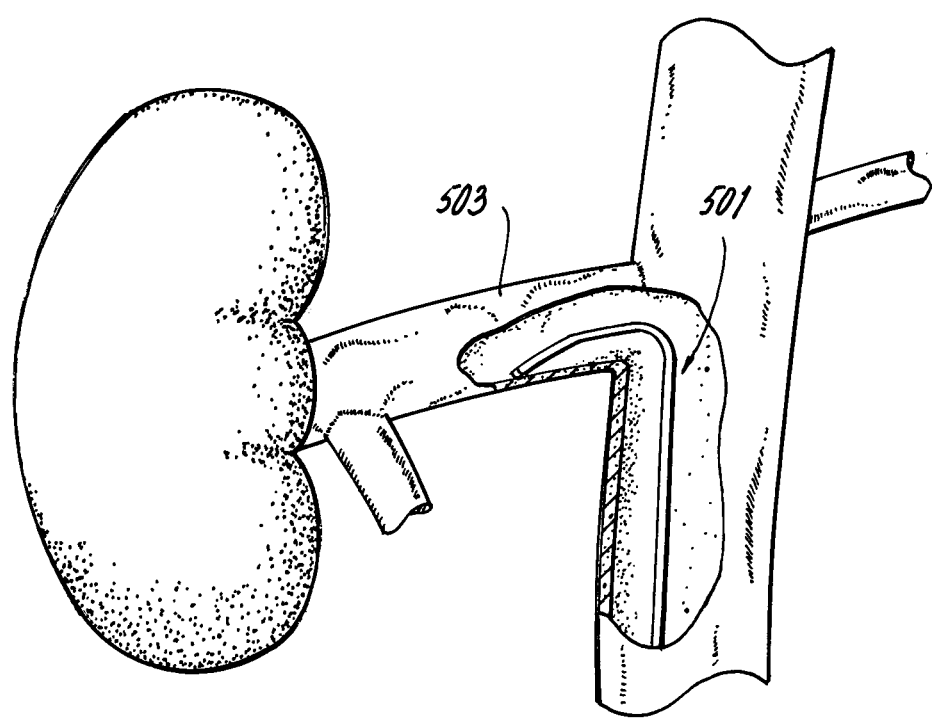
FIG. 5 is an in-situ view of an embodiment of this disclosure disposed within a renal artery during a medical procedure.

Referring to FIG. 5, an embodiment of a steerable guiding sheath 501, similar to any embodiment disclosed herein, is shown in situ in a renal artery 503.

The devices, methods, and systems of the present disclosure, as described above and shown in the drawings, provide for steerable medical devices with superior properties including advanced directional and precision control. While the apparatus and methods of the subject disclosure have been shown and described with reference to embodiments, those skilled in the art will readily appreciate that changes and/or modifications may be made thereto without departing from the spirit and scope of the subject disclosure.

What is claimed is:

1. A steerable medical device, comprising:
 a) a sheath defining a longitudinal axis having a deflectable distal end portion, and at least one lateral passage extending therethrough and configured to accommodate at least one steering cable; and
 b) a steering handle operatively associated with a proximal end portion of the sheath and having an actuation mechanism operatively connected to the at least one steering cable accommodated within the at least one lateral passages of the sheath for steering the deflectable distal end portion of the sheath in at least one direction relative to the longitudinal axis thereof, wherein the steering handle includes a lock surface with a cam protrusion extending therefrom, and a lock protrusion extending from the cam protrusion, wherein the actuation mechanism includes a central hub having a friction lock cavity, wherein a friction lock member is positioned within the friction lock cavity between the lock surface and the actuation mechanism for rotation with respect to the lock surface, wherein the friction lock member includes at least one camming surface that abuts the cam protrusion of the lock surface to allow for variable frictional resistance to relative rotation of the central hub, and wherein the at least one camming surface includes at least one locking divot to engage with the lock protrusion of the lock surface to prevent unwanted rotation between the lock surface and the friction lock member and to provide tactile feedback when rotating the friction lock member.

2. The steerable device of claim 1, wherein the at least one lateral passage includes two diametrically opposed lateral passages and the at least one steering cable includes two steering cables, one associated with each lateral passage.

3. The steerable device of claim 2, wherein the sheath includes a central lumen extending therethrough.

4. The steerable device of claim 3, wherein a hemostatic seal is operatively associated with the proximal end portion of the sheath such that the hemostatic seal is in fluid communication with the central lumen.

5. The steerable device of claim 3, wherein the central lumen of the sheath is configured to receive at least one medical device therethrough.

6. The steerable device of claim 5, wherein the sheath has an outer diameter size ranging from about 4 F to about 18 F.

7. The steerable device of claim 5, wherein the proximal end portion of the sheath extends through the steering handle to a proximal end thereof.

8. The steerable device of claim 5, wherein the sheath includes a tubular section reinforced with at least one of braiding, mesh, or wires.

9. The steerable device of claim 5, further comprising a flexible dilator dimensioned for introduction through the central lumen of the sheath and having an axial passage extending therethrough for accommodating a flexible guide wire.

10. The steerable device of claim 9, further comprising a flexible guide wire for introduction through the axial passage of the flexible dilator.

11. The steerable device of claim 10, wherein the dilator includes depth markings disposed along a length of the dilator for indicating how deep the dilator is inserted into the central lumen of the sheath.

12. The steerable device of claim 1, wherein the sheath includes a hydrophobic coating on an exterior surface thereof.

13. The steerable device of claim 1, wherein the sheath includes a soft atraumatic tip portion disposed at the distal end portion.

14. The steerable device of claim 1, wherein the distal end portion of the sheath includes a radiopaque marker band for determining the location of the distal end of the sheath in situ.

15. The steerable device of claim 1, wherein an infusion port is operatively associated with the proximal end portion of the sheath.

16. The steerable device of claim 15, wherein the distal end portion of the sheath includes at least two side holes in fluid communication with the infusion port for introducing fluid through the distal end portion of the sheath.

17. A steering handle for a steerable medical device, the steering handle configured for effectuating bi-directional steering of the sheath, the steering handle including:
 an actuation mechanism operatively connectable to at least one steering cable of the steerable medical device, wherein the actuation mechanism includes diametrically opposed actuators extending from a central hub operatively connectable to the two or more steering wires, wherein the central hub includes a friction lock cavity;
 a lock surface with a cam protrusion extending therefrom, and a lock protrusion extending from the cam protrusion; and
 a friction lock member is positioned within the friction lock cavity between the lock surface and the actuation mechanism for rotation with respect to the lock surface, wherein the friction lock member includes at least one camming surface that abuts the cam protrusion of the lock surface to allow for variable frictional resistance to relative rotation of the central hub, and wherein the at least one camming surface includes at least one locking divot to engage with the lock protrusion of the lock surface to prevent unwanted rotation between the lock surface and the friction lock member and to provide tactile feedback when rotating the friction lock member.

18. A kit for placing a surgical device in the vasculature of patient, comprising:
   a) an enclosure; and
   b) a steerable medical device disposed within the enclosure, wherein the steerable medical device includes:
      i) a sheath having a deflectable distal end portion, and at least one lateral passage configured to accommodate at least one steering cable; and
      ii) a steering handle operatively associated with a proximal end portion of the sheath and having an actuation mechanism operatively connected to the at least one steering cable accommodated within the at least one lateral passages of the sheath for steering the deflectable distal end portion of the sheath in at least one direction, wherein the steering handle includes a lock surface with a cam protrusion extending therefrom, and a lock protrusion extending from the cam protrusion, wherein the actuation mechanism includes a central hub having a friction lock cavity, wherein a friction lock member is positioned within the friction lock cavity between the lock surface and the actuation mechanism for rotation with respect to the lock surface, wherein the friction lock member includes at least one camming surface that abuts the cam protrusion of the lock surface to allow for variable frictional resistance to relative rotation of the central hub, and wherein the at least one camming surface includes at least one locking divot to engage with the lock protrusion of the lock surface to prevent unwanted rotation between the lock surface and the friction lock member and to provide tactile feedback when rotating the friction lock member.

19. The kit of claim 18, further comprising a dilator disposed within the enclosure configured to be inserted into the sheath.

20. The kit of claim 18, further comprising a guide wire disposed within the enclosure.

* * * * *